United States Patent [19]

ten Haken et al.

[11] 4,239,889

[45] Dec. 16, 1980

[54] 3-(N-HETEROCYCLYL)ISOXAZOLIDINE FUNGICIDES

[75] Inventors: Pieter ten Haken, Eastling; Shirley B. Webb, Sheldwich, near Faversham, both of England

[73] Assignee: Shell Oil Company, Houston, Tex.

[21] Appl. No.: 48,424

[22] Filed: Jun. 14, 1979

[30] Foreign Application Priority Data

Jun. 27, 1978 [GB] United Kingdom ............... 27979/78

[51] Int. Cl.$^3$ .......................................... C07D 413/04

[52] U.S. Cl. ................... 544/335; 424/250; 424/251; 544/336

[58] Field of Search ................................ 544/335, 336

[56] References Cited

U.S. PATENT DOCUMENTS

| 4,066,770 | 1/1978 | Boyce et al. ................ 424/168 |
| 4,138,402 | 2/1979 | Boyce et al. ................ 546/275 |

*Primary Examiner*—Paul M. Coughlan, Jr.

[57] ABSTRACT

Certain 2-p-halopenyl-3-(heterocyclyl)-5-substituted-isoxazolidines, are useful for controlling barley powdery mildew disease.

4 Claims, No Drawings

3-(N-HETEROCYCLYL)ISOXAZOLIDINE FUNGICIDES

DESCRIPTION OF THE INVENTION

It has been found that useful fungicidal properties are possessed by 3-(N-heterocyclyl)-2-phenylisoxazolidines of the formula

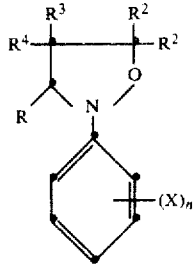
(I)

wherein R is a pyrazinyl or pyrimidinyl moiety, $R^1$, $R^2$, $R^3$ and $R^4$ each is hydrogen, substituted or non-substituted hydrocarbyl or hydrocarbyloxy, with the proviso that $R^2$ and/or $R^4$ also can represent cyano, nitro, acyloxy, phenylsulphonyl, arylthio or a phosphorus-containing group, substituted or non-substituted amino, or amino-, alkyl-, or alkoxy-carbonyl, and with the further proviso that $R^1$, together with $R^2$ and the interjacent carbon atom, or together with $R^3$ and the interjacent carbon atoms, respectively, form a carbocyclic or heterocyclic ring, X represents halogen, nitro, cyano, substituted or non-substituted alkyl, alkoxy or aryl, hydroxy, optionally substituted amino, alkoxycarbonyl, alkylsulphenyl, acyl, optionally substituted phenoxy, acyloxy, or heterocyclyl, and n is 0, 1, 2 or 3.

The N-heteroaromatic moiety represented by R may be unsubstituted or it may be substituted, by one or more substituents bonded to carbon atoms, and including hydrocarbyl groups, in particular alkyl groups of up to 5 carbon atoms, and alkoxy groups, preferably methyl groups.

$R^1$ preferably is hydrogen or alkoxy, suitable methoxy or ethoxy. $R^1$ may also by aryl, alkyl with up to 5 carbon atoms, in particular methyl, or a phosphorus-containing group such as an alkoxyphosphonyl group, e.g., diethoxyphosphonyl.

$R^2$, $R^3$ and $R^4$ each preferably is hydrogen, or alkyl of up to 5 carbon atoms, suitably methyl or ethyl. Preferably, $R^3$ is alkoxyalkyl, such as methoxymethyl or ethoxymethyl. Preferably, X is alkanoyl, alkoxycarbonyl, substituted or non-substituted phenoxy, or halogen, in particular chlorine or fluorine, substituted at the carbon atom in the 4-position of the ring relative to the carbon atom bonded to the indicated nitrogen atom.

It will be appreciated that the isoxazolidines of Formula I contain at least one asymmetric carbon atom, with three such centers of asymmetry being possible when the substituents $R^1$ and $R^3$ are different from $R^2$ and $R^4$, respectively, and hence these derivatives can exist in a number of different geometric and optical isomeric forms. All such geometric and optical isomers, together with physical and racemic mixtures of these isomers that are active, are within the scope of the invention.

The isoxazolidines of Formula I can be prepared by reacting a nitrone of the formula:

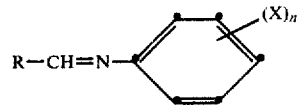
(II)

with an olefin of the formula:

(III)

wherein the symbols have the same meanings as in Formula I. The nitrone starting material may be prepared by suitable adaptation of known procedures (e.g., as described in *Bull. Soc. Chim. Fr.*, 1967, page 4179). Suitably, the reaction can be carried out by refluxing the reactants in an inert solvent, such as benzene, toluene, methylene chloride, for an appropriate length of time at atmospheric pressure, or higher pressures. In certain instances wherein $R^2$ represents a substituted alkyl group, for example, an alkylthioalkyl group, the desired compound may most conveniently be prepared by further reacting an isoxazolidine of Formula I wherein $R^2$ is, for example, a chloromethyl group.

The invention includes the compounds of Formula I, per se, fungicidal compositions containing them, and their use for protecting crops from attack by fungi, in which crops subject to or subjected to such attack, seeds of such crops or soil in which such crops are growing or to be grown are treated with a fungicidally effective amount of at least one of the compounds of Formula I, preferably in the form of a composition together with a carrier, with a surface-active agent or both a carrier and a surface active agent.

The term "carrier" as used herein means a solid or fluid material, which my be inorganic or organic and of synthetic or natural origin, with which the acitve compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols, ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–15% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may contain other ingredients, for example, protective colloids such as gelatin, glue, casin, gums, cellulose ethers, and polyvinyl alcohol; thixotropic agents, e.g., bentonites, sodium polyphosphates; stabilizers such as ethylene diamine tetra-acetic acid, urea, triphenyl phosphate, other fungicides or pesticides; and stickers, for example non-volatile oils.

The compositions of the invention may also contain other biologically active ingredients, for example, other compounds possessing pesticidal, especially insecticidal, acaricidal, herbicidal or fungicidal properties.

The method of applying the compounds of this invention comprises applying a compound of Formula I, ordinarily in a composition of one of the aforementioned types, to a locus or area to be protected from undesirable fungi, such as the foliage of the plants or the plant growth medium, e.g., soil in which the plant is growing or is to be grown. The active compound, of course, is applied in amounts sufficient to exert the desired action.

The amount of compound of the invention to be used in controlling undesirable fungi will naturally depend on the fungi that are involved, the formulation used, the mode of application, the climate, the season of the year, and other variables. Recommendations as to precise amounts are, therefore, not possible. In general, however, application to the locus to be protected of from 0.1 to 10.0 kilograms per hectare of the compound used in this invention will be satisfactory.

The invention is illustrated in the following examples. In each case, the identities of the product, and of any intermediates of the product, were confirmed by appropriate chemical and spectral analyses.

Example 1

2-p-chlorophenyl-3-(pyrazin-2'-yl)-5-ethoxy isoxazolidine (1)

To a solution of 7 g of pyrazin-2-yl-N-p-chlorophenyl nitrone in 100 ml of dry benzene was added 20 ml of ethylvinyl ether. The mixture was stirred and heated under reflux for 48 hours. Solvent and excess vinylethyl ether were removed under reduced pressure, and the residue was subjected to column chromatography on silica gel, eluting with ether. The product thus obtained was recrystallized from 40/60 petroleum spirit to give (1), as a colorless solid, mp: 52°–52.5° C.

EXAMPLE 2

By procedures similar to those described in Example 1, 2-p-chlorophenyl-3-(2'-pyrazinyl)-5,5'-dimethyl isoxazolidine (2) was prepared as a solid, mp: 59°–60° C.

EXAMPLE 3

2-p-chlorophenyl-3-(pyrimidin-5'-yl)-5-ethoxy isoxazolidine (2)

To a solution of 3.95 g of pyrimidin-5-yl-N-p-chlorophenyl nitrone in 100 ml of dry benzene was added 15 ml of vinylethyl ether. The mixture was stirred and heated under reflux for 24 hours. Solvent and excess vinylethyl ether were removed under reduced pressure, and the residue was subjected to column chromatography on silica gel, eluting with ether. 3 was obtained as an oil.

Fungicidal activity of compounds of the invention was determined as follows:

Activity against barley powdery mildew (Erysiphe graminos).

The test measures the direct antisporulant activity of compounds applied as a foliar spray. For each compound, about 40 barley seedlings were grown to the one-leaf stage in a plastic pot containing sterile potting compost. Inoculation was effected by dusting the leaves with conidia of Erysiphe graminis. 24 hours after inoculation the seedlings were sprayed with a solution of the compound in a mixture of acetone (50%), surfactant (0.054%) and water using a track sprayer. The rate of application was equivalent to 1 kilogram of active material per hectare. First assessment of disease was made 5 days after treatment, when the overall level of sporulation on treated pots were compared with that on control pots.

The extent of disease control is set out on the table below, expressed as a control rating according to the criteria:

0 = less than 50% disease control
1 = 50–80% disease control
2 = greater than 80% disease control

| Compound | Activity Against Barley Powdery Mildew Disease Control |
|---|---|
| 1 | 2 |
| 2 | 2 |
| 3 | 2 |

We claim:

1. A compound of the formula

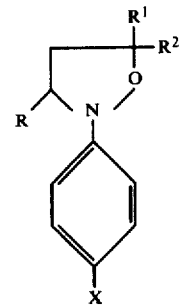

wherein R is 2-pyrazinyl or 5-pyrimidinyl, X is chlorine or fluorine, and
  (a) $R^1$ is hydrogen and $R^2$ is alkoxy of one or two carbon atoms, or
  (b) $R^1$ and $R^2$ each is methyl.

2. A compound according to claim 1 wherein X is chlorine, R is pyrazin-2-yl, $R^1$ is hydrogen and $R^2$ is ethoxy.

3. A compound according to claim 1 wherein X is chlorine, R is pyrimidin-5-yl, $R^1$ is hydrogen and $R^2$ is ethoxy.

4. A compound according to claim 1 wherein X is chlorine, R is pyrazin-2-yl, and $R^1$ and $R^2$ each is methyl.

* * * * *